(12) United States Patent
Teles et al.

(10) Patent No.: US 8,362,296 B2
(45) Date of Patent: Jan. 29, 2013

(54) PROCESS FOR PREPARING 4-PENTENOIC ACID

(75) Inventors: Joaquim Henrique Teles, Otterstadt (DE); Michael Schelper, Ludwigshafen (DE); Kai Gumlich, Mannheim (DE); Mathieu Chabanas, Niederlauterbach (FR); Christian Müller, Mannheim (DE); Anton Meier, Birkenheide (DE)

(73) Assignee: BASF SE (DE)

( * ) Notice: Subject to any disclaimer, the term of this patent is extended or adjusted under 35 U.S.C. 154(b) by 341 days.

(21) Appl. No.: 12/859,622

(22) Filed: Aug. 19, 2010

(65) Prior Publication Data

US 2011/0046413 A1    Feb. 24, 2011

(30) Foreign Application Priority Data

Aug. 21, 2009  (EP) .................................. 09168353

(51) Int. Cl.
*C07C 51/235* (2006.01)
(52) U.S. Cl. ........................ 562/532; 562/533
(58) Field of Classification Search .................. None
See application file for complete search history.

(56) References Cited

U.S. PATENT DOCUMENTS

| | | | |
|---|---|---|---|
| 4,071,563 A | 1/1978 | Kummer et al. | |
| 4,097,523 A | 6/1978 | Kao et al. | |
| 5,849,257 A | 12/1998 | Fujiwara et al. | |
| 2010/0018389 A1 | 1/2010 | Baumann et al. | |

FOREIGN PATENT DOCUMENTS

| | | |
|---|---|---|
| DE | 2517447 A1 | 7/1976 |
| GB | 782430 A | 9/1957 |
| WO | WO-98/25698 A1 | 6/1998 |
| WO | WO-2008/017342 A1 | 2/2008 |
| WO | WO-2008/071632 A2 | 6/2008 |
| WO | WO-2009/121706 A1 | 10/2009 |
| WO | WO-2009/121707 A1 | 10/2009 |
| WO | WO-2010/023211 A2 | 3/2010 |

OTHER PUBLICATIONS

N. I. Kapustina et al., "Oxidation of Secondary Cyclic Alcohols by Pb(OAc)4 Catalyzed by Cu(II) Compounds", Russion Chemical Bulletin, vol. 37, No. 10, pp. 2095-2099, 1989.
E. V. Starokon et al., "High-Temperature Carboxidation of Cyclopentene With Nitrous Oxide", Kinetics and Catalysis, vol. 48, No. 3, pp. 376-380, 2007.
Jianchun Xie et al., "Synthesis of Flavor 2-Pentenoic Acid", Shipin Kexue, vol. 28, No. 10, pp. 252-254, 2007.
International Search Report for PCT/EP2010/062098 mailed on Jun. 30, 2011.
Notificiation of Transmittal of Translation of the Interntional Preliminary Report on Patentability for PCT/EP2010/062098 dated Mar. 19, 2012.

*Primary Examiner* — Yevegeny Valenrod
(74) *Attorney, Agent, or Firm* — Connolly Bove Lodge & Hutz LLP

(57) ABSTRACT

The present invention relates to a process for preparing 4-pentenoic acid, at least comprising the oxidation of a mixture (G) comprising 4-pentenal, 3-methyl-2-butanone and cyclopentene oxide, and to the use of a mixture (G) comprising 4-pentenal, 3-methyl-2-butanone and cyclopentene oxide for preparing 4-pentenoic acid. In the context of the present invention, the mixture (G) is preferably obtained as a byproduct of the oxidation of cyclopentene to cyclopentanone by means of dinitrogen monoxide.

7 Claims, 1 Drawing Sheet

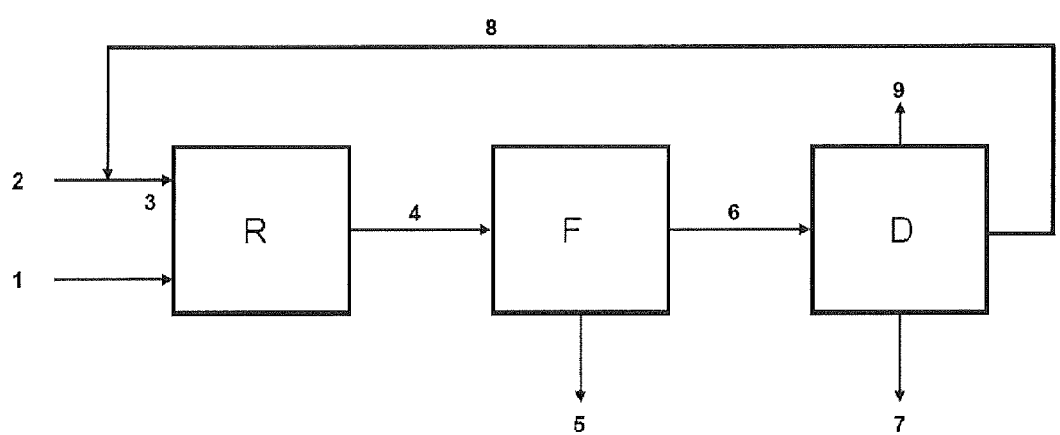

PROCESS FOR PREPARING 4-PENTENOIC ACID

CROSS-REFERENCE TO RELATED APPLICATIONS

This application claims benefit to European application 09 168 353.2, filed Aug. 21, 2009.

BACKGROUND OF THE INVENTION

The present invention relates to a process for preparing 4-pentenoic acid, at least comprising the oxidation of a mixture (G) comprising 4-pentenal, 3-methyl-2-butanone and cyclopentene oxide, and to the use of a mixture (G) comprising 4-pentenal, 3-methyl-2-butanone and cyclopentene oxide for preparing 4-pentenoic acid. In the context of the present invention, the mixture (G) is preferably obtained as a by-product of the oxidation of cyclopentene to cyclopentanone by means of dinitrogen monoxide.

4-Pentenoic acid and its esters find use as odorants and flavorings, especially in milk and cheese products. In addition, 4-pentenoic acid and 4-pentenoates are also known as pharmacologically active substances which are capable of inducing hypoglycemia (see, for example, H. Sherratt, H. Osmundsen, *Biochemical Pharmacology* (1976) 25(7), 743-750).

It is known from the prior art that 4-pentenoic acid can be prepared by reacting diethyl malonate with allyl chloride in the presence of a base and subsequent hydrolysis, decarboxylation and acidification (see J. Xie, B. Sun, S. Sha, F. Zheng, W. Dang, *Beijing Gongshang Daxue Xuebao, Ziran Kexueban* (2007), 25(1), 7-9). However, this synthesis has the disadvantage that the reaction proceeds from relatively expensive feedstocks and utilizes them only poorly (loss of $CO_2$). At a described yield of approx. 70%, about 340 kg of reactants, namely diethyl malonate and allyl chloride, are required to prepare 100 kg of 4-pentenoic acid.

The prior art additionally discloses the principle of the oxidation of unsaturated aldehydes with oxygen to give the corresponding carboxylic acids. For example, the oxidation of alpha,beta-unsaturated aldehydes is described. For example, WO 2008/017342 describes the oxidation of citronellal to citronellic acid with oxygen in the presence of a supported gold catalyst. U.S. Pat. No. 4,097,523 describes the oxidation of alpha,beta-unsaturated aldehydes with oxygen in the presence of thallium as a catalyst. Other homogeneous catalysts, for example manganese, copper or cobalt, are also known in the oxidation of alpha,beta-unsaturated aldehydes with oxygen ("Crotonaldehyde and Crotonic acid", R. P. Schulz, J. Blumenstein, C. Kohlpaintner in "Ullmann's Encyclopedia of Industrial Chemistry", 7th edition, online Release 2008). However, none of these prior art documents provides any indication that these methods are applicable to the oxidation of alpha,beta-unsaturated aldehydes to other unsaturated aldehydes.

Proceeding from this prior art, it was an object of the present invention to provide a process of economic interest for preparing 4-pentenoic acid.

It has been found that, surprisingly, 4-pentenoic acid can be prepared in good yields and high purity by the oxidation of 4-pentenal.

A significant factor in the economic viability of the oxidation process is the availability of 4-pentenal. 4-Pentenal can be prepared, for example, by Claisen isomerization of allyl vinyl ether (see, for example, R. F. Webb, A. J. Duke, J. A. Parsons, *J. Chem. Soc.* (1961), 4092-4095). However, allyl vinyl ether is not a commercially available vinyl ether and is thus not readily available industrially either.

Alternatively, 4-pentenal can also be prepared by the thermolysis of acetaldehyde diallyl acetal, as described in DE 25 17 447. However, this method has the disadvantage that allyl alcohol has to be recycled, a significant proportion of which decomposes to propionaldehyde, which makes the process uneconomic in turn.

The prior art further discloses that 4-pentenal forms as a by-product in the preparation of cyclopentanone by oxidation of cyclopentene with dinitrogen monoxide ($N_2O$) (see, for example, E. V. Starokon', K. S. Shubnikov, K. A. Dubkov, A. S. Kharitonov, G. I. Panov, Kinetics and Catalysis (2007), 48(3), 376-380). However, the 4-pentenal is not obtained as a pure substance but as a mixture with other by-products from the cyclopentanone synthesis.

BRIEF SUMMARY OF THE INVENTION

It has been found that, surprisingly, even such contaminated 4-pentenal can be oxidized selectively. The present invention therefore offers the great advantage that no distillative removal of pure 4-pentenal is needed before the corresponding use thereof, which is all the more advantageous in that the boiling points of 4-pentenal (98.5° C.), cyclopentene oxide (100.8° C.) and 3-methyl-2-butanone (94.4° C.) are very close to one another and hence a distillative purification of 4-pentenal is possible only with a high level of complexity.

The present invention therefore relates to a process for preparing 4-pentenoic acid, at least comprising step (a)

(a) oxidizing a mixture (G) comprising 4-pentenal, 3-methyl-2-butanone and cyclopentene oxide.

DETAILED DESCRIPTION OF THE INVENTION

As already mentioned above, it has been found that, surprisingly, even such contaminated 4-pentenal can be oxidized selectively and the process according to the invention can prepare 4-pentenoic acid in high yields and high purity.

According to the invention, in step (a), a mixture (G) comprising 4-pentenal, 3-methyl-2-butanone and cyclopentene oxide is oxidized to obtain 4-pentenoic acid. According to the invention, the process may comprise further steps, for example purification steps.

A mixture (G) which comprises 4-pentenal, 3-methyl-2-butanone and cyclopentene oxide and is suitable as a reactant for the process according to the invention may comprise 4-pentenal, 3-methyl-2-butanone and cyclopentene oxide in different ratios. The mixture (G) may also comprise further compounds. Suitable mixtures (G) are obtained, for example, as a by-product in the oxidation of cyclopentene to cyclopentanone.

For example, the mixture (G) may comprise 10 to 90% by weight of 4-pentenal, preferably 25 to 90% by weight, especially 40 to 85% by weight, more preferably 50 to 75% by weight, of 4-pentenal.

In a further embodiment, the present invention therefore also relates to a process for preparing 4-pentenoic acid as described above, wherein the mixture (G) comprises 10 to 90% by weight of 4-pentenal.

In principle, in the context of the present invention, the oxidation in step (a) can be effected in any suitable manner known to those skilled in the art. Preference is given, however, to using an oxygenous gas mixture as the oxidizing agent, for example air, oxygen or a mixture comprising oxygen and an inert gas such as nitrogen or argon.

In a further embodiment, the present invention therefore also relates to a process for preparing 4-pentenoic acid as described above, wherein an oxygenous gas mixture is used as the oxidizing agent for the oxidation in step (a).

According to the invention, the oxidation in step (a) can be performed either with or without solvent. Preference is given to performing the oxidation in the presence of a solvent. The solvent is preferably a carboxylic acid. Particularly preferred solvents are 4-pentenoic acid, 2-ethylhexanoic acid, isononanoic acid, for example a technical mixture which comprises 3,5,5-trimethylhexanoic acid as the main component, propylheptanoic acid, for example a technical mixture which comprises 2-propyl-heptanoic acid as the main component, or neodecanoic acid, for example a technical mixture of double-alpha-branched carboxylic acids having 10 carbon atoms.

In a further embodiment, the present invention therefore also relates to a process for preparing 4-pentenoic acid as described above, wherein the oxidation in step (a) is performed in the presence of a solvent.

More particularly, the present invention also relates to a process for preparing 4-pentenoic acid as described above, wherein the oxidation in step (a) is performed in the presence of a solvent selected from the group consisting of 4-pentenoic acid, 2-ethylhexanoic acid, isononanoic acid, propylheptanoic acid and neodecanoic acid. Equally possible are suitable mixtures of two or more of these solvents.

In an alternative embodiment, the present invention also relates to a process for preparing 4-pentenoic acid as described above, wherein the oxidation in step (a) is performed without solvent.

The oxidation in step (a) can be performed either with or without catalysts. The catalysts used may, for example, be transition metals from the group of Cr, Mn, Fe, Ni, Cu, Tl in the form of salts or complexes thereof, or alkali metal and alkaline earth metal salts selected from the group consisting of hydroxides, carbonates, hydrogencarbonates and carboxylates. Preference is given to performing the oxidation in step (a) without addition of, i.e. in the absence of, a catalyst. In general, the present invention therefore relates to a process as described above, wherein the oxidation in step (a) is performed in the absence of a catalyst selected from the group consisting of Cr, Mn, Fe, Ni, Cu, Tl in the form of salts or complexes thereof and alkali metal and alkaline earth metal salts selected from the group consisting of alkaline earth metal hydroxides, carbonates, hydrogencarbonates and carboxylates. More particularly, the present invention relates to a process as described above, wherein the oxidation in step (a) is performed in the absence of a catalyst.

In a further embodiment, the present invention thus relates to a process for preparing 4-pentenoic acid as described above, wherein the oxidation in step (a) is performed without addition of a catalyst.

As already stated, the process according to the invention, as well as step (a), may comprise further steps, for example purification steps. For instance, it is possible in accordance with the invention that step (a) is followed by a further step in order to concentrate the resulting 4-pentenoic acid. One suitable example of the concentration mentioned is a distillation.

According to the invention, the mixture (G) used may be any desired mixture comprising 4-pentenal, 3-methyl-2-butanone and cyclopentene oxide.

Preferably, in the context of the present invention, the mixture (G) used is a mixture obtained as a by-product of the oxidation of cyclopentene to cyclopentanone. This process regime has the advantage that the by-product mixture obtained need not be purified in a complex manner, but can be used as such in the process according to the invention, thus making the process inexpensive.

In a further embodiment, the present invention therefore also relates to a process for preparing 4-pentenoic acid as described above, wherein the mixture (G) is obtained as a by-product of the oxidation of cyclopentene to cyclopentanone.

According to the invention, it is possible that the mixture which comprises 4-pentenal, 3-methyl-2-butanone and cyclopentene oxide and is obtained as a by-product of the oxidation of cyclopentene to cyclopentanone is used directly in the oxidation in step (a) of the process according to the invention. However, it is also possible in principle that a mixture obtained as a by-product of the oxidation of cyclopentene to cyclopentanone is first treated suitably before use in step (a). For example, this mixture, before step (a), can be concentrated and/or the proportion of other components which disrupt step (a) and/or subsequent steps in the mixture can be reduced.

Especially suitable is the oxidation of cyclopentene to cyclopentanone by means of dinitrogen monoxide, since this oxidation forms, as a by-product, mixtures which can be used in the oxidation in step (a) without complex purification.

In a further embodiment, the present invention therefore also relates to a process for preparing 4-pentenoic acid as described above, wherein cyclopentene is oxidized to cyclopentanone in the presence of dinitrogen monoxide.

The oxidation of cyclopentene to cyclopentanone, especially the oxidation of cyclopentene to cyclopentanone by means of dinitrogen monoxide, in the context of the present invention can in principle be effected by any suitable process.

Cyclopentene can in principle originate from any desired source. Cyclopentene in the context of the present invention may be used as a pure substance or in a mixture with further compounds, especially hydrocarbons. The proportion of hydrocarbons, for example cyclopentane, may, for example, be in the range from 2 to 80% by weight, preferably 20 to 70% by weight, more preferably 40 to 60% by weight, based in each case on the mixture used.

For example, the mixture comprises 20 to 98% by weight, preferably 30 to 80% by weight, more preferably 40 to 60% by weight, based in each case on the overall mixture, of cyclopentene, and 2 to 80% by weight, preferably 20 to 70% by weight, more preferably 40 to 60% by weight, of cyclopentane.

The content of other components in the mixture is, for example, less than 15% by weight, preferably less than 12% by weight, preferentially less than 10% by weight, especially less than 8% by weight, more preferably less than 5% by weight.

In addition to the hydrocarbons, the mixture may also comprise at most 5% by weight, preferably at most 2% by weight, of at least one further compound, for example a compound selected from the group consisting of aldehydes, ketones, epoxides and mixtures thereof. These compounds may be present in the reaction mixture with the proviso that they do not disrupt the reaction of cyclopentene with dinitrogen monoxide.

In addition to cyclopentene, it is accordingly possible for at least one further $C_5$ hydrocarbon, for example n-pentane and/or cyclopentane, or at least one hydrocarbon with more than 5 carbon atoms, for example cyclohexane, or a mixture of at least one further $C_5$ hydrocarbon and at least one hydrocarbon with more than 5 carbon atoms, to be present in the mixture.

The cyclopentene used or the mixture comprising cyclopentene preferably originates from a steamcracker. In this context, preference is given, for example, to $C_5$ cuts from steamcracker plants which comprise essentially only $C_5$ and $C_6$ hydrocarbons. Hydrocarbons with more than 6 carbon atoms are typically not present in the $C_5$ cuts obtained on the industrial scale. These $C_5$ cuts obtained on the industrial scale comprise, as well as cyclopentene, for example, 2-butene, isopentane, 1-pentene, 2-methylbutene-1, trans-2-pentene, n-pentane, cis-2-pentene, 2-methylbutene-2, cyclopentane, 2,2-dimethylbutane, 2-methylpentane, 3-methylpentane, n-hexane and benzene. In general, a $C_5$ cut from a steamcracker plant comprises cyclopentene in the range from 5 to 60% by weight and preferably in the range from 15 to 50% by weight. Such mixtures are advantageously purified further before they are used.

Preference is given in accordance with the invention to using cyclopentene which originates from a partly hydrogenated cracker cut, for example a partly hydrogenated $C_5$ cut from a naphtha cracker. In this context, "partly hydrogenated" means that the $C_5$ cut has been hydrogenated until it is substantially free of dienes.

This cut is preferably divided, in a first distillation column, into a top stream and a bottom stream, the top stream preferably comprising only a small amount of cyclopentene, preferably less than 10% by weight, more preferably less than 5% by weight, of cyclopentene. The bottom stream preferably comprises a small amount of 2-methyl-2-butene, preferably less than 5% by weight, more preferably less than 1% by weight and most preferably less than 0.5% by weight of 2-methyl-2-butene. The distillation is performed, for example, at a pressure between 0.5 and 10 bar, preferably between 1 and 5 bar and more preferably between 2 and 4 bar. The first column preferably has a total of at least 70 plates, at least 18 plates preferably being located in the rectifying section and at least 52 plates in the stripping section. The separating elements used may, for example, be trays or packings. Preference is given to using packings.

The bottom stream of this first column is preferably used as the feed for a second column. In the second column, the top stream obtained is the purified cyclopentene. The top product preferably comprises at least 80% by weight of cyclopentene, preferentially at least 90% by weight of cyclopentene and more preferably at least 95% by weight of cyclopentene. The principle secondary component present in the top stream is cyclopentane. Other secondary components present therein are, for example, 2-methyl-2-butene, 2,2-dimethylbutane, n-pentane, trans-2-pentene or cis-2-pentene. The bottom product of the second column preferably comprises not more than 20% by weight of cyclopentene, preferably not more than 10% by weight and more preferably not more than 5% by weight of cyclopentene. This bottom product comprises cyclopentane as the principle component, preferably at least 50% by weight of cyclopentane. In addition to cyclopentane as the principle component and residues of cyclopentene, this stream also comprises, for example, 2-methylpentane, 3-methylpentane, methylcyclopentane, 1-hexene, 2,2-dimethylbutane, n-hexane, benzene and 2-methyl-2-butene as secondary components.

It is, however, also possible that a dividing wall column is used instead of the two columns described above. A suitable dividing wall column has, for example, a total of 100 theoretical plates. The dividing wall is, for example, located in the center and spans, for example, the range between the $27^{th}$ and $94^{th}$ plates. In this case, the feed is preferably added on the inlet side of the dividing wall at the level of plate 42; the discharge is preferably on the outlet side of the dividing wall at the level of plate 54. The reflux ratio is, for example, in the range from 5 to 7, preferably from 5.5 to 6.5, for example about 6.0. The 95% cyclopentane can thus be obtained in the side draw. In such an embodiment, top and bottom streams preferably each comprise less than 2% by weight of cyclopentene.

The cyclopentene thus obtained can be oxidized with dinitrogen monoxide.

The dinitrogen monoxide used may in principle originate from any desired source. It is possible to use pure dinitrogen monoxide. However, it is equally possible to use dinitrogen monoxide which has been obtained in pure form or as a mixture by a purification process.

Both in the preparation of dinitrogen monoxide and in the use of offgas streams, $N_2O$ is typically obtained initially as a dilute gaseous mixture with other components. These components can be divided into those which have a disruptive effect for specific applications and those which behave inertly. For use as an oxidizing agent, gases having a disruptive effect include $NO_x$ or, for example, oxygen ($O_2$). The term "$NO_x$", as understood in the context of the present invention, refers to all compounds $N_aO_b$ where a is equal to 1 or 2 and b is a number from 1 to 6, where $N_aO_b$ is not $N_2O$. Instead of the term "$NO_x$", the term "nitrogen oxides" is also used in the context of the present invention. Disruptive secondary components also include $NH_3$ and organic acids.

Suitable purification processes for dinitrogen monoxide are described, for example, in WO 2008/071632, or in European patent applications EP 08153953.8 and EP 08153952.0.

A suitable process for purifying a gas mixture comprising dinitrogen monoxide is, for example, a process at least comprising the steps of (A) treating a gas mixture G-0 comprising dinitrogen monoxide to obtain a gas mixture G-A, at least comprising the steps of
 (i) absorbing the gas mixture G-0 in a solvent mixture S-I to obtain an offgas stream and a composition C-A
 (ii) desorbing a gas mixture G-1 from the composition C-A to obtain a solvent mixture S-I'
(B) condensing the gas mixture G-A to obtain a liquid composition C-1 comprising dinitrogen monoxide and a gaseous mixture G-K, wherein the gaseous mixture G-K is recycled into the treatment in step (A). Such a process and preferred configurations are described, for example, in the above-cited EP 08153952.0.

The process comprises a step (A), comprising steps (i) and (ii). In step (A), a gas mixture G-0 comprising dinitrogen monoxide is treated to obtain a gas mixture G-A, step (A) comprising at least steps (i) and (ii). In step (i), the gas mixture G-0 is absorbed in a solvent mixture S-I to obtain an offgas stream and a composition C-A. In step (ii), a gas mixture G-1 is desorbed from the composition C-A to obtain a solvent mixture S-I'.

The gas mixture G-0 is a gas mixture comprising dinitrogen monoxide. The gas mixture G-0 may comprise further components as well as dinitrogen monoxide and may in principle originate from any source.

The term "gas mixture" as used in the context of the present invention refers to a mixture of two or more compounds which are in the gaseous state at ambient pressure and ambient temperature. At altered temperature or altered pressure, the gas mixture may also be present in another state of matter, for example liquid, and is still referred to as a gas mixture in the context of the present invention.

In the context of the present invention, the composition of the gas mixtures or of the liquefied gas mixtures, unless explicitly stated otherwise, is specified in % by volume. The data relate to the composition of the gas mixtures at ambient pressure and ambient temperature.

In principle, the composition of the mixtures may be determined in any way known to those skilled in the art. In the context of the present invention, the composition of the gas mixtures is preferably determined by gas chromatography. However, it may also be determined by means of UV spectroscopy, IR spectroscopy or by wet chemical methods.

When a gas mixture G-0 is used, its content of dinitrogen monoxide is substantially arbitrary, as long as it is guaranteed that the above-described purification is possible.

The $N_2O$-containing gas mixtures which are used as gas mixture G-0 for this process generally have an $N_2O$ content between 2 and 80% by volume of $N_2O$. It further comprises, for example, 2 to 21% by volume of $O_2$ and up to 30% by volume of $NO_x$ as undesired components. In addition, it may also comprise varying amounts of $N_2$, $H_2$, $CO_2$, CO, $H_2O$, $NH_3$, and traces of organic compounds may also be present. For example, the gas mixture G-0 may also comprise 9 to 13% by volume of $N_2$ and up to 5.5% by volume of $NH_3$. The sum of the components of the gas mixture G-0 adds up to 100% by volume.

In one possible embodiment of the process, a gas mixture G-0 comprising at least 3% by volume of dinitrogen monoxide is used, but preference is given in turn to using mixtures having a dinitrogen monoxide content in the range from 4 to 60% by volume, more preferably in the range from 5 to 25% by volume and especially preferably in the range from 6 to 18% by volume.

In this embodiment, the gas mixture G-0 has, for example, an $N_2O$ content of 6 to 18% by volume, more preferably, for example, 7% by volume, 8% by volume, 9% by volume, 10% by volume, 11% by volume, 12% by volume, 13% by volume, 14% by volume, 15% by volume, 16% by volume or 17% by volume.

The gas mixture G-0 has, for example, a $CO_2$ content of 0.1 to 7.5% by volume, preferably of 0.5 to 5% by volume, more preferably of 1 to 2.5% by volume. At the same time, the gas mixture G-0 has, for example, an $O_2$ content of 1 to 10% by volume, preferably of 2 to 7.5% by volume, more preferably, for example, 3.0 to 6% by volume. In addition, the gas mixture G-0 may also comprise 50 to 95% by volume of $N_2$, preferably 60 to 90% by volume, more preferably 70 to 85% by volume, and also further components, for example nitrogen oxides or solvent residues. $NO_x$ may, for example, be present in an amount of 0 to 0.2% by volume, preferably 0.0001 to 0.15% by volume, more preferably 0.0005 to 0.1% by volume. The sum of the components of the gas mixture G-0 adds up to 100% by volume.

In a further embodiment, the gas mixture G-0 comprising dinitrogen monoxide is at least one dinitrogen monoxide-comprising offgas of a chemical process. This also comprises embodiments in which at least two nitrogen monoxide-comprising offgases of a single plant serve as the gas mixture comprising dinitrogen monoxide. Equally included are embodiments in which at least one dinitrogen monoxide-comprising offgas of one plant and at least one further dinitrogen monoxide-comprising offgas of at least one further plant serve as the gas mixture comprising dinitrogen monoxide.

The term "gas mixture comprising dinitrogen monoxide" refers both to embodiments in which the offgas mentioned is subjected to the inventive purification process in unmodified form and to embodiments in which at least one of the offgases mentioned is subjected to a modification.

The term "modification" as used in this context refers to any suitable process by which the chemical composition of a gas mixture is altered. Accordingly, the term "modification" comprises, inter alia, embodiments in which a dinitrogen monoxide-comprising offgas is concentrated with regard to the dinitrogen monoxide content in at least one suitable process. Preference is given to not subjecting the offgas to any modification.

In a further embodiment, the chemical composition of an offgas may also be altered by adding pure dinitrogen monoxide to the offgas.

The gas mixture G-0 comprising $N_2O$ which is used may, for example, be an offgas from an industrial process. It preferably originates from an offgas of a plant for preparing carboxylic acids by oxidation of alcohols, aldehydes or ketones with nitric acid, for example from an adipic acid plant, a dodecanedicarboxylic acid plant or a glyoxal plant, from the offgas of a nitric acid plant which uses the above offgas streams as a reactant, from the offgas of a plant for the partial oxidation of $NH_3$ or from the offgas of a plant which uses the gas mixtures generated therein, for example a hydroxylamine plant.

It is also possible to use a mixture of different offgases.

For example, the at least one dinitrogen monoxide-comprising offgas originates from an adipic acid plant, a dodecanedicarboxylic acid plant, a glyoxal plant, a hydroxylamine plant and/or a nitric acid plant, the latter in turn preferably being operated with at least one offgas of an adipic acid plant, of a dodecanedicarboxylic acid plant or of a glyoxal plant.

For example, the offgas stream of an adipic acid plant is used, in which generally 0.8 to 1.0 mol of $N_2O$ per mole of adipic acid formed is formed by oxidation of cyclohexanol/cyclohexanone mixtures with nitric acid. As described, for example, in A. K. Uriarte et al., *Stud. Surf. Sci. Catal.* (2000) 130 p. 743-748, the offgases of adipic acid plants also comprise different concentrations of further constituents including nitrogen, oxygen, carbon dioxide, carbon monoxide, nitrogen oxides, water and volatile organic compounds.

The abovementioned dodecanedicarboxylic acid plant is substantially of an identical plant type.

An example of a typical composition of an offgas of an adipic acid plant or of a dodecanedicarboxylic acid plant is reproduced in the following table:

| Component | Concentrations/ % by weight |
|---|---|
| $NO_x$ | 19-25 |
| $N_2O$ | 20-28 |
| $N_2$ | 30-40 |
| $O_2$ | 7-10 |
| $CO_2$ | 2-3 |
| $H_2O$ | ~7 |

The offgas stream of an adipic acid plant or of a dodecanedicarboxylic acid plant may be used directly in the purification process.

In a further embodiment, the offgas stream of a nitric acid plant is used which is fed fully or partly with offgases comprising dinitrogen monoxide and nitrogen oxides from other processes. In such nitric acid plants, nitrogen oxides are adsorbed and for the most part converted to nitric acid, while dinitrogen monoxide is not converted. For example, such a nitric acid plant may be supplied by nitrogen oxides which are prepared by selective combustion of ammonia and by offgases of an adipic acid plant and/or by offgases of a dodecanedicarboxylic acid plant and/or by offgases of a glyoxal plant. It is equally possible to supply such a nitric acid plant solely by offgases of an adipic acid plant and/or by offgases of a dodecanedicarboxylic acid plant and/or by offgases of a glyoxal plant.

The offgases of such nitric acid plants always comprise varying concentrations of still further constituents including nitrogen, oxygen, carbon dioxide, carbon monoxide, nitrogen oxides, water and volatile organic compounds.

An example of a typical composition of an offgas of such a nitric acid plant is reproduced in the following table:

| Component | Concentrations/ % by weight |
|---|---|
| $NO_x$ | <0.1 |
| $N_2O$ | 4-36 |
| $N_2$ | 57-86 |
| $O_2$ | 3-9 |
| $CO_2$ | 1-4 |
| $H_2O$ | ~0.6 |

The offgas stream of a nitric acid plant may be used directly in such a purification process.

In a further embodiment, the offgas stream of a hydroxylamine plant is used, in which, for example, ammonia is initially oxidized with air or oxygen to give NO, and small amounts of dinitrogen monoxide are formed as a by-product. The NO is subsequently hydrogenated with hydrogen to give hydroxylamine. Since dinitrogen monoxide is inert under the hydrogenation conditions, it accumulates in the hydrogen circuit. In preferred process versions, the purge stream of a hydroxylamine plant comprises dinitrogen monoxide in the range from 9 to 13% by volume in hydrogen. This purge stream may be used as such for the inventive purification. It is equally possible to concentrate this stream in a suitable manner with regard to the dinitrogen monoxide content as described above.

It is equally possible to selectively prepare dinitrogen monoxide for use in the purification process. Preference is given inter alia to the preparation via the thermal decomposition of $NH_4NO_3$, as described, for example, in U.S. Pat. No. 3,656,899. Preference is likewise further given to the preparation via the catalytic oxidation of ammonia, as described, for example, in U.S. Pat. No. 5,849,257 or in WO 98/25698.

In the absorption in step (i), the gas mixture G-0 is absorbed in a solvent mixture S-I. Any method of absorption known to those skilled in the art can be used in principle. This affords an offgas stream and a composition C-A. The composition C-A is then treated further in step (ii). The gas mixture G-1 is desorbed from the composition C-A to obtain a solvent mixture S-I'.

The gas mixture G-1 comprises at least dinitrogen monoxide and may comprise further components.

The solvent mixture S-I used may be any suitable solvent mixture known to those skilled in the art, provided that it is ensured that the gas mixture G-0, especially dinitrogen monoxide, is at least partly absorbed.

In step (A), a gas mixture G-A comprising dinitrogen monoxide is obtained. The gas mixture G-A may additionally comprise further components. When step (A) does not comprise any further steps after step (ii), the composition of the gas mixture G-1 is identical to that of the gas mixture G-A.

In step (B), the gas mixture G-A obtained from step (A) is at least partly condensed to obtain a liquid composition C-1 comprising dinitrogen monoxide and a gaseous mixture G-K. The liquid composition C-A comprises dinitrogen monoxide and may comprise further components. The gaseous mixture G-K comprises preferably only small amounts of dinitrogen monoxide. In this process, after the condensation in step (B), the gaseous mixture G-K is recycled into the treatment in step (A).

This process may comprise further steps. For example, it is possible that further steps are included between steps (A) and (B).

Equally, step (A) may also comprise further steps. More particularly, it is possible that step (A) comprises a further absorption of the gas mixture G-1 in a suitable solvent mixture and a further desorption:

(iii) absorbing the gas mixture G-1 in a solvent mixture S-II to obtain an offgas stream and a composition C-B
(iv) desorbing a gas mixture G-2 from the composition C-B to obtain a solvent mixture S-II'.

The solvent mixture S-II used may be any suitable solvent mixture known to those skilled in the art, provided that it is ensured that the gas mixture G-1, especially dinitrogen monoxide, is at least partly absorbed.

When step (A) does not comprise any further steps after step (iv), the composition of gas mixture G-2 is identical to that of gas mixture G-A.

It is equally possible that step (A), as well as steps (i) and (ii), or as well as steps (i), (ii), (iii) and (iv), comprises further steps, for example including further absorptions and desorptions.

As described above, the gaseous mixture G-K obtained in step (B) is recycled into step (A) of the process. The gaseous mixture G-K is mixed with another gas mixture. The gaseous mixture G-K is preferably recycled into step (A) such that recovery of the dinitrogen monoxide which may be present in the gaseous mixture G-K is possible. It is therefore preferred that the gaseous mixture G-K is mixed with a gas mixture which is sent to an absorption, especially gas mixture G-0 or gas mixture G-1. It is thus preferred in the context of the present invention to recycle the gaseous mixture G-K into step (i) or into step (iii) of step (A).

The solvent mixtures S-I and/or S-II used may be any suitable solvent mixture known to those skilled in the art, provided that it is ensured that especially dinitrogen monoxide is absorbed.

Suitable solvent mixtures S-I and S-II for the absorption in step (i) or (iii) are those which have a better solubility for $N_2O$ and preferably also $CO_2$ as an inert component than for the undesired components of the incoming reactant gas G-0.

For instance, the solvent mixtures S-I and/or S-II used may be organic solvents or aqueous solvent mixtures. The organic solvents used may be any solvents in which the ratio between $N_2O$ solubility (in mol/mol of solvent) and the solubility of the undesired secondary components under the conditions existing in the absorber (this ratio is referred to hereinafter as "gamma") is at least 5. This ratio may be determined for each individual component present in the gas mixture. Preferred organic solvents have, for example at 30° C., a gamma($O_2$) value of 6 to 30, preferably 9 to 25, and a gamma($N_2$) value of greater than 10, preferably of greater than 15, in particular of greater than 20.

Examples of suitable organic solvents are, for example, aliphatic hydrocarbons, preferably having at least 5 carbon atoms, more preferably having at least 8 carbon atoms, substituted or unsubstituted aromatic hydrocarbons, esters, ethers, amides, lactones, lactams, nitriles, alkyl halides, olefins or mixtures of these solvents.

Very particular preference is given to organic solvents which have a boiling point at standard pressure of at least 100° C., since this reduces the solvent losses both in the offgas stream of the absorber and of the desorber.

In addition, suitable solvents simultaneously have a good solubility for dinitrogen monoxide. The solubility is specified by the ratio between the partial pressure of $N_2O$ in the gas phase and the molar proportion of $N_2O$ in the liquid phase (Henry coefficient, $H_{N2O}$), i.e. a small value means a high solubility of dinitrogen monoxide in the solvent. This ratio for an organic solvent used in the first step in particular at 30° C. is preferably less than 1000, more preferably less than 750, particularly preferably less than 500, in particular less than 150.

Suitable organic solvents include N-methylpyrrolidone, dimethylformamide, dimethyl sulfoxide, propylene carbonate, sulfolane, N,N-dimethylacetamide or cyclopentane. Particular preference is given in the context of the present invention, for example, to toluene, nitrobenzene, 1,2-dichlorobenzene, tetradecane, for example a technical-grade mixture of saturated hydrocarbons having predominantly 14 carbon atoms, and dimethyl phthalate.

It is equally possible to use aqueous solvent mixtures as solvent mixtures S-I and/or S-II. In principle, the above remarks apply for the suitability of the solvent mixtures for the process. In particular, the solvent mixtures S-I and/or S-II used may be solvent mixtures at least comprising 50% by weight of water based on the overall solvent mixture. It is also possible in the context of the present invention that the pH of the solvent mixture used is set within a particular range. According to the invention, a suitable pH for an aqueous solvent mixture is, for example, in the range from 2.0 to 8.0. It is also possible in accordance with the invention that the pH of the solvent mixtures S-I or S-II used in the individual absorption steps is varied.

The pH is measured with a commercially available glass electrode which has been ii calibrated beforehand against a buffer of known pH. All pH data are based on a measurement with a calibrated and temperature-compensated glass electrode. If the calibration temperature differs from the measurement temperature, a temperature compensation is used. This definition and this method correspond to the currently valid IUPAC recommendation (R. P. Buck et al., *Pure Appl. Chem.* (2002) 74(11), p. 2169-2200 and especially section 11 thereof).

Water has a high selectivity for the desired components, especially dinitrogen monoxide and carbon dioxide. At the same time, the absolute solubility of dinitrogen monoxide in water is sufficient to achieve further concentration. Water as a solvent has the advantage that, even under pressure in the presence of concentrated dinitrogen monoxide, no safety problems occur. At the same time, no contamination of the gas mixture G-2 with an organic solvent can occur, which would necessitate additional purification steps.

Therefore, both solvent mixture S-I and S-II may be an organic solvent mixture or an aqueous solvent mixture. It is possible that the solvent mixture S-I used is an organic solvent and the solvent mixture S-II used is an aqueous solvent mixture. It is equally possible that the solvent mixture S-I used is an aqueous solvent mixture and the solvent mixture S-II an organic solvent. Both solvent mixture S-I and solvent mixture S-II are preferably an aqueous solvent mixture.

It is additionally preferred that, when the solvent mixture S-I and/or S-II used is an aqueous solvent mixture, the pH of the aqueous solvent mixture is set within a particular range.

For example, the pH of the aqueous solvent mixture in the absorption may preferably be in the range from 3.5 to 8.0. At this pH, according to the invention, there is a good absorption of dinitrogen monoxide and carbon dioxide in the solvent mixture, while other gases which may be present in the gas mixture G-0 are absorbed to a small degree, if at all. The pH is preferably within a range from 5.0 to 7.5, more preferably within a range from 6.0 to 7.0.

The pH is measured before or during the contacting of the gas mixture with the aqueous solvent mixture and then, for example, the pH is adjusted by suitable measures. It is equally possible that no measures are needed to adjust the pH.

In principle, the pH can be adjusted by all measures known to those skilled in the art. Suitable measures for adjusting the pH are, for example, addition of an acid or alkali or addition of further solvents.

For example, the pH of the aqueous solvent mixture is measured before or after the absorption and the pH is set within the range specified by suitable measures. The pH can be measured continuously or discontinuously.

When the pH of solvent mixture S-I and of solvent mixture S-II is adjusted, the pH of solvent mixture S-I and of solvent mixture S-II can be adjusted independently of one another. For instance, it is also possible that only the pH of solvent mixture S-I or of solvent mixture S-II is adjusted. However, it is also possible for the pH of solvent mixture S-I and of solvent mixture S-II to be adjusted within the same range.

An aqueous solvent mixture is understood to mean a solvent mixture at least comprising 50% by weight of water, for example 50 to 100% by weight of water, preferably at least 60% by weight of water, especially at least 70% by weight of water, more preferably at least 80% by weight of water, for example at least 90% by weight of water. The aqueous solvent mixture preferably comprises at least 90% by weight of water, based in each case on the overall aqueous solvent mixture.

This aqueous solvent mixture, in addition to water, may also comprise other polar water-miscible solvents, for example glycols. In addition, the aqueous solvent mixture, as well as water, may also comprise dissolved salts, for example salts of the alkali metals or alkaline earth metals, especially hydroxides, hydrogencarbonates, carbonates, nitrates, nitrites, sulfates, hydrogenphosphates or phosphates.

For example, the content of salts in the aqueous solvent mixture is less than 5% by weight, preferably less than 2.5% by weight, more preferably less than 2.0% by weight. The content of salts in the aqueous solvent mixture is, for example, 0.0001 to 5% by weight, preferably 0.001 to 2.5% by weight, especially 0.01 to 2.0% by weight.

The content of salts in the aqueous solvent mixture is preferably controlled by continuously or discontinuously replacing a portion of the solvent mixture laden with salts with an appropriately adjusted amount of fresh solvent mixture.

In step (i), according to the invention, there is an at least partial absorption of the gas mixture G-0 in a solvent mixture S-I to obtain a composition C-A and an offgas stream depleted of the absorbed gases.

A depleted offgas stream is understood to mean a gas stream which comprises the gases not absorbed in the absorption in the solvent mixture S-I or S-II.

The composition C-A comprises the solvent mixture S-I and the gases absorbed therein.

When the solvent mixture S-I used is water, the composition C-A comprises, for example, 90.0 to 99.9999% by weight of water, especially 95.0 to 99.999% by weight and preferably 98.0 to 99.99% by weight of water; for example 0.01 to 0.25% by weight of dinitrogen monoxide, especially 0.05 to 0.2% by weight and preferably 0.1 to 0.15% by weight of dinitrogen monoxide; for example 0.0001 to 0.1% by weight of carbon dioxide, especially 0.001 to 0.05% by weight of carbon dioxide; for example 0.0001 to 0.1% by weight of nitrogen, especially 0.001 to 0.05% by weight of nitrogen; for example 0.05 to 1.5% by weight of sodium nitrite, especially 0.1 to 1.0% by weight and preferably 0.25 to 0.75% by weight of sodium nitrite; for example 0.05 to 1.5% by weight of sodium nitrate, especially 0.1 to 1.0% by weight and preferably 0.25 to 0.75% by weight of sodium nitrate; for example 0.0001 to 0.1% by weight of sodium hydrogencarbonate, especially 0.001 to 0.05% by weight of sodium hydrogencarbonate; and traces of oxygen and argon. The sum of the components of composition (A) adds up to 100% by weight.

This depleted offgas stream comprises, for example, 0.1 to 2.0% by volume of argon, especially 0.25 to 1.5% by volume and preferably 0.5 to 1.0% by volume of argon; for example 1.0 to 10% by volume of oxygen, especially 2.5 to 7.5% by volume and preferably 4.0 to 6.0% by volume of oxygen; for example 1.0 to 10% by volume of dinitrogen monoxide, especially 2.5 to 7.5% by volume and preferably 4.0 to 6.0% by volume of dinitrogen monoxide; for example 70 to 99.9% by volume of nitrogen, especially 75 to 95% by volume and preferably 80 to 90% by volume of nitrogen; for example 0.01 to 0.5% by volume of carbon monoxide, especially 0.05 to 0.25% by volume and preferably 0.08 to 0.1% by volume of carbon monoxide; for example 0.1 to 1.5% by volume of carbon dioxide, especially 0.25 to 1.0% by volume and preferably 0.5 to 0.75% by volume of carbon dioxide; for example 0.1 to 1.5% by volume of water, especially 0.25 to 1.0% by volume and preferably 0.5 to 0.75% by volume of water. The sum of the components of the offgas stream adds up to 100% by volume.

Preference is given to performing step (i) of the process continuously. This means that the solvent mixture S-I and the gas mixture G-0 are contacted continuously, which continuously forms the composition C-A and the depleted offgas stream.

In the absorption in step (i), preferably dinitrogen monoxide and carbon dioxide are absorbed. For example, it is also possible for nitrogen, oxygen and argon to be absorbed. Nitrogen oxides $NO_x$ are also absorbed in step (i).

The process further comprises a step (ii) in which a gas mixture G-1 is desorbed from the composition C-A to obtain a solvent mixture S-I'.

In step (ii), preferably dinitrogen monoxide and carbon dioxide are desorbed from the composition C-A.

As well as the solvent mixture S-I used, the solvent mixture S-I' also comprises as yet undesorbed gases and conversion products.

For example, in the case that the solvent mixture S-I is used with a particular adjusted pH and the pH is adjusted by adding an alkali, especially sodium hydroxide solution, the solvent mixture S-I' comprises, for example, 90.0 to 99.9999% by weight of water, especially 95.0 to 99.999% by weight and preferably 98.0 to 99.99% by weight of water; for example 0.001 to 0.1% by weight of dinitrogen monoxide, for example 0.05 to 1.5% by weight of sodium nitrite, especially 0.1 to 1.0% by weight and preferably 0.25 to 0.75% by weight of sodium nitrite; for example 0.05 to 1.5% by weight of sodium nitrate, especially 0.1 to 1.0% by weight and preferably 0.25 to 0.75% by weight of sodium nitrate; for example 0.0001 to 0.1% by weight of sodium hydrogencarbonate, especially 0.001 to 0.05% by weight of sodium hydrogencarbonate. The solvent mixture S-I' may additionally also comprise further compounds. The sum of the components of the solvent mixture S-I' adds up to 100% by weight.

The gas mixture G-1 has, for example, an $N_2O$ content of 40 to 80% by volume, preferably of 45 to 75% by volume, especially of 50 to 65% by volume, more preferably, for example, 51% by volume, 52% by volume, 53% by volume, 54% by volume, 55% by volume, 56% by volume, 57% by volume, 58% by volume, 59% by volume, 60% by volume, 61% by volume, 62% by volume, 63% by volume, 64% by volume or 65% by volume.

The gas mixture G-1 has, for example, a $CO_2$ content of 5 to 15% by volume, preferably 6 to 12% by volume, more preferably, for example, 7% by volume, 9% by volume, 10% by volume or 11% by volume. At the same time, the gas mixture G-1 has, for example, an $O_2$ content of 1.0 to 4.0% by volume, preferably 1.5 to 3.5% by volume, more preferably 2.5 to 3.1% by volume, for example 2.6% by volume, 2.7% by volume, 2.8% by volume, 2.9% by volume or 3.0% by volume. In addition, the gas mixture G-1 may also comprise 20 to 40% by volume of $N_2$, preferably 20 to 35% by volume, and also further components, for example nitrogen oxides. $NO_x$ may be present, for example, in an amount of 0 to 0.1% by volume, preferably 0.0001 to 0.01% by volume, more preferably 0.0002 to 0.05% by volume. The sum of the components of the gas mixture G-1 adds up to 100% by volume. The gas mixture G-1 may additionally comprise 0 to 10% by volume of water, especially 2 to 8% by volume and preferably 4 to 6% by volume of water.

The process may further comprise one step (iii) and one step (iv). In the absorption in step (iii), there is an absorption in a solvent mixture S-II to obtain a composition C-B and an offgas stream depleted of the absorbed gases. The composition C-B comprises the solvent mixture S-II and the gases absorbed therein.

When the solvent mixture S-II used is water, the composition C-B comprises, for example, 90.0 to 99.9999% by weight of water, especially 95.0 to 99.999% by weight and preferably 98.0 to 99.99% by weight of water; for example 0.01 to 2.5% by weight of dinitrogen monoxide, especially 0.1 to 1.5% by weight and preferably 0.5 to 1.0% by weight of dinitrogen monoxide; for example 0.001 to 0.5% by weight of carbon dioxide, especially 0.01 to 0.25% by weight of carbon dioxide; for example 0.0001 to 0.1% by weight of nitrogen, especially 0.001 to 0.05% by weight of nitrogen; and traces of oxygen and argon. The sum of the components of the composition C-B adds up to 100% by weight.

Preference is given to performing step (iii) continuously. This means that the solvent mixture S-II and the gas mixture G-1 are contacted continuously, which continuously forms the composition C-B and the depleted offgas stream. Preferably 60 to 80% of the entering gas stream are absorbed in step (iii).

The process preferably further comprises a step (iv) in which a gas mixture G-2 is desorbed from the composition C-B to obtain a solvent mixture S-II'. In step (iv), preference is given to desorbing dinitrogen monoxide and carbon dioxide from the composition C-B. As well as the solvent mixture S-II used, the solvent mixture S-II' comprises as yet undesorbed gases and conversion products.

The resulting gas mixture G-2 comprises at least 50% by volume of $N_2O$, more preferably at least 60% by volume of $N_2O$ and most preferably at least 75% by volume of $N_2O$. Typically, gas mixture G-2 comprises up to 99% by volume of $N_2O$, especially up to 97% by volume of $N_2O$, for example up to 96% by volume of $N_2O$, up to 95% by volume of $N_2O$, up to 94% by volume of $N_2O$, up to 93% by volume of $N_2O$, up to 92% by volume of $N_2O$, up to 91% by volume of $N_2O$, up to 90% by volume of $N_2O$ or else up to 85% by volume of $N_2O$.

The gas mixture G-2 has, for example, an $N_2O$ content of 60 to 95% by volume, preferably 70 to 90% by volume, especially 75 to 85% by volume, more preferably, for example, 76% by volume, 77% by volume, 78% by volume, 79% by volume, 80% by volume, 81% by volume, 82% by volume, 83% by volume, 84% by volume or 85% by volume.

The gas mixture G-2 has, for example, a $CO_2$ content of 1 to 20% by volume, preferably of 5 to 15% by volume, more preferably, for example, 6% by volume, 7% by volume, 8% by volume, 9% by volume, 10% by volume, 11% by volume, 12% by volume, 13% by volume or 14% by volume. At the same time, the gas mixture G-2 has, for example, an $O_2$ content of 0.01 to 5.0% by volume, preferably of 0.1 to 2.5% by volume, more preferably, for example, 0.2 to 1.0% by volume. In addition, the gas mixture G-2 may also comprise 0.1 to 10% by volume of $N_2$, preferably 0.5 to 5% by volume, and also further components, for example nitrogen oxides or solvent residues. At the same time, the gas mixture G-2 comprises less than 1% by volume of $O_2$, especially less than 0.5% by volume of $O_2$, less than 0.5% by volume of $NO_x$. $NO_x$ may be present, for example, in an amount of 0 to 0.1% by volume, preferably 0.0001 to 0.01% by volume, more preferably 0.0002 to 0.02% by volume. The sum of the components of the gas mixture G-2 adds up to 100% by volume.

When step (A) comprises no further steps after step (iv), the composition of gas mixture G-A corresponds to the composition of gas mixture G-2.

Both solvent mixture S-I' and solvent mixture S-II' may be recycled at least partly into the process. In this case, it is possible that solvent mixture S-I' and/or solvent mixture S-II' is/are recycled into the process at least partially as solvent mixture S-I or S-II. Solvent mixture S-I' and/or solvent mixture S-II' can especially be treated before it is used again in the process as solvent mixture S-I or S-II.

More particularly, it is also possible that only a portion of solvent mixture S-I' and/or S-II' is used again in the process and is admixed, for example, with water or another solvent in order then to be used again in the process as solvent mixture S-I and/or S-II. The absorption in step (i) or (iii) of the process described can in principle be effected by all methods known to those skilled in the art. More particularly, the absorption in the solvent mixture can be brought about by increasing the pressure of the reactant gas or by lowering the temperature of the solvent mixture or by a combination of the measures stated.

In step (i) or (iii) of the process, preference is given to first compressing the gas mixture, for example to a pressure of 10 to 35 bar, preferentially 13 to 30 bar, preferably 14 to 25 bar. Subsequently, the compressed gas mixture is preferably contacted at this pressure with the solvent mixture S-I in step (i) or in the solvent mixture S-II in step (iii).

The absorption in step (i) and step (iii) is effected in equipment (absorbers) in which a gas-liquid phase interface is generated, through which mass and heat transfer between the phases is enabled, and which are provided if required with internal or external equipment for heat supply and/or heat removal.

The phases within the absorber can be conducted in cocurrent, in countercurrent, or in a combination thereof.

The absorption can be effected in one or more stages, preferably in one stage. In the absorption, the absorber used is preferably a device with a plurality of theoretical plates, especially 2 to 8 theoretical plates, more preferably 3 to 6.

Possible embodiments of the absorber are in each case columns with trays, for example bubble-cap trays or sieve trays, columns with structured internals, for example structured packings, columns with unstructured internals, for example random packings, or apparatus in which the liquid phase is present in dispersed form, for example as a result of spraying in nozzles, or a combination of the embodiments mentioned.

The desorption of the gas mixture G-1 or G-2 from the composition C-A or composition C-B in step (ii) or (iv) of the process can be brought about by lowering the pressure over the solvent mixture, increasing the temperature of the solvent mixture, or by stripping with solvent vapor, or a combination thereof.

The demands on the equipment (desorbers) for the desorption of the gas mixture G-1 or G-2 from the composition C-A or composition C-B, and the conduction of the phases, are analogous to those in the absorber, i.e. suitable equipment is that in which a gas-liquid phase interface is generated, through which heat and mass transfer between the phases is enabled, and which are provided if required with internal or external equipment for heat supply and/or heat removal.

The desorption can be performed in one or more stages. Possible embodiments of the desorber are a simple (flash) vessel and columns.

A preferred embodiment in which the absorption, i.e. the contacting with the solvent mixture, and the desorption are combined in one apparatus is, for example, the dividing wall column. In this column, the contacting, and the associated absorption, and the desorption are conducted in countercurrent in a plurality of stages by varying the temperature, combined with stripping with solvent vapor. Both in (i) and (ii) and in (iii) and (iv), the absorption and desorption apparatus can be combined, especially in a dividing wall column.

In a particularly preferred embodiment, in step (i), the gas mixture G-0 comprising $N_2O$ is first contacted under elevated pressure p(absorption) with the solvent mixture S-I in an absorption column operated in countercurrent and with random packing, which can result in absorption, and a composition C-A is obtained. In step (ii), the composition C-A, in this embodiment, is transferred into a vessel in which the composition C-A is decompressed to a lower pressure p(desorption)<p(absorption). The process is preferably conducted virtually isothermally with a temperature difference between absorption and desorption temperature of not more than 20 K, preferably not more than 15 K, especially not more than 10 K. The absorption pressure here is 1 to 100 bar, preferably 5 to 65 bar, especially 10 to 40 bar, preferably 10 to 35 bar, more preferably 13 to 30 bar, even more preferably about 14 to 25 bar, and the desorption pressure 0.1 to 2 bar absolute, preferably 0.5 to 1.5 bar absolute, more preferably 1.0 to 1.2 bar absolute.

Preference is likewise given, in step (iii), to first contacting the gas mixture G-1 under elevated pressure p(absorption) with a solvent mixture S-II in an absorption column operated in countercurrent and with random packing to obtain the composition C-B. In step (iv), composition C-B is transferred to a vessel in which the composition C-B is decompressed to a lower pressure p(desorption)<p(absorption). The process is preferably likewise conducted virtually isothermally with a temperature difference between the absorption and desorption temperatures of not more than 20 K, preferably not more than 15 K, especially not more than 10 K. The absorption pressure here is 1 to 100 bar, preferably 5 to 65 bar, especially 10 to 40 bar, preferably 10 to 35 bar, more preferably 13 to 30 bar, even more preferably about 14 to 25 bar, and the desorption pressure 0.1 to 2 bar absolute, preferably 0.5 to 1.5 bar absolute, more preferably 1.0 to 1.2 bar absolute.

In addition to steps (i), (ii), (iii) and (iv), step (A) of the process may also comprise further steps. For example, the process may also comprise a further treatment of the gas mixture G-1 between steps (ii) and (iii). Such treatments comprise, for example, a change in the temperature or a change in the pressure or a change in the temperature and in the pressure.

For example, the composition of a gas mixture may change, for example through condensation of one of the components. These components may, for example, be water or another compound present in the solvent mixture S-I, preferably a solvent which is used for step (i) in the solvent mixture S-I in the process.

For instance, it is possible that further components are removed from the gas mixture G-1 or G-2. For example, it is possible that traces of water, which may be present in the gas mixture G-2 in step (iv) after the desorption, are removed from the gas mixture G-2 by compression and subsequent cooling.

In this case, the gas mixture G-2 is advantageously compressed to a pressure of 1 to 35 bar, preferably 2 to 30 bar, more preferably 3 to 27 bar. Cooling is preferably effected subsequently, preferably to 1 to 25° C., more preferably 3 to 20° C., especially 4 to 15° C., more preferably 8 to 12° C.

After step (A), a condensation of the gas mixture G-A obtained in step (A) is performed in step (B). This affords a liquid composition C-1 comprising dinitrogen monoxide and a gaseous mixture G-K, said gaseous mixture G-K preferably being recycled into the treatment in step (A).

The condensation in step (B) of the process can in principle be effected by any suitable process known to those skilled in the art. It is preferred that the gas mixture G-A is at least partially condensed. 20 to 99% by weight, preferably 50 to 90% by weight and most preferably 60 to 80% by weight of the gas mixture G-A is condensed.

The gaseous mixture G-K comprises, for example, 70 to 90% by volume of dinitrogen monoxide, especially 75 to 85% by volume, more preferably 78 to 82% by volume. The gaseous mixture G-K further comprises, for example, 4 to 18% by volume of carbon dioxide, especially 6 to 16% by volume and more preferably 8 to 12% by volume of $CO_2$. The gaseous mixture G-K further comprises, for example, 0.01 to 5% by volume of oxygen, especially 0.5 to 3% by volume and more preferably 1.0 to 2.0% by volume of oxygen, and, for example, 0 to 1% by volume of argon, where the sum of the components of the gaseous mixture G-K adds up to 100% by volume.

Preferably in step (B), the gas mixture G-A is first compressed and then cooled. The gas mixture G-A is advantageously compressed to a pressure of 1 to 35 bar, preferably 2 to 30 bar, more preferably 3 to 27 bar. Cooling is preferably effected subsequently, preferably to 10 to –70° C., more preferably 8 to –30° C., especially 5 to –25° C.

When step (B) of the process is preceded by a step in which an already compressed gas mixture is obtained, step (B) preferably does not comprise a further compression.

The process for purifying a gas mixture comprising dinitrogen monoxide may also comprise further steps. For instance, it is also possible that the process comprises further steps after step (B).

For example, in the process, the composition C-1 can be treated further. It is more particularly possible that there is a further step for concentration of the composition C-1. In principle, all suitable methods known to those skilled in the art for further concentration of the composition C-1 or for removal of impurities, for example of residues of solvent, are possible.

For instance, the process comprises especially a further step (C) for removal of impurities from the composition C-1. Preferably, in step (C), the composition C-1 comprising dinitrogen monoxide is contacted with a gas mixture M-1 to obtain a composition C-2 and a gas mixture M-2.

The gas mixture M-1 used may in principle be all substances which have a lower boiling point than dinitrogen monoxide or mixtures thereof. Preference is given to using gases which do not react with dinitrogen monoxide, for example nitrogen, helium, neon, argon, krypton, xenon, hydrogen, carbon monoxide, methane and tetrafluoromethane. Preference is given to using nitrogen.

For the treatment in step (C), it is possible to use any apparatus suitable for contacting gases and liquids with one another. The examples here include bubble columns, for example operated in cocurrent or countercurrent, with or without random packing or structured packing, in trickle or liquid-phase mode, stirred tanks, for example with sparging stirrers, or the like. The treatment in step (C) can be effected either batchwise or continuously. Preference is given to performing it continuously.

The treatment in step (C) is preferably performed at a temperature between –90° C. and +37° C., preferably at a temperature between –80° C. and 0° C. Preference is given to performing the treatment in step (C) at a pressure which is at least as high as the vapor pressure of the liquid composition C-1 at the selected temperature and at not more than 100 bar. Preference is given to selecting a pressure which 0.2 to 5 bar above the pressure at which the absorption is conducted.

The amount of gas mixture M-1 used must be sufficiently great to achieve the desired oxygen depletion but, on the other hand, as small as possible in order to avoid losses of dinitrogen monoxide. Typically between 5 and 100 mol of gas mixture M-1 are used per mole of oxygen in the liquid composition C-1, preferably between 15 and 30 mol of gas mixture M-1 per mole of oxygen in the liquid composition C-1.

In step (C), a liquid composition C-2 is obtained, whose oxygen content has been reduced further compared to the liquid composition C-1.

This composition C-2 comprises, for example, 75 to 95% by volume of dinitrogen monoxide, especially 80 to 90% by volume, more preferably 82 to 88% by volume. The composition C-2 further comprises, for example, 4 to 18% by volume of carbon dioxide, especially 6 to 16% by volume and more preferably 8 to 12% by volume of $CO_2$. The composition C-2 further comprises, for example, 0.01 to 1.0% by volume of oxygen, especially 0.05 to 0.5% by volume and more preferably 0.1 to 0.4% by volume of oxygen, and, for example, 0 to 1% by volume of nitrogen, where the sum of the components of the composition C-2 adds up to 100% by volume.

In step (C), a gas mixture M-2 is also obtained, which, in addition to the gas mixture M-1, may comprise further components, for example oxygen.

This gas mixture M-2 comprises, for example, 70 to 90% by volume of dinitrogen monoxide, especially 75 to 85% by volume, more preferably 77 to 82% by volume. The gas mixture M-2 additionally comprises, for example, 4 to 18% by volume of carbon dioxide, especially 6 to 16% by volume and more preferably 8 to 12% by volume of $CO_2$. The gas mixture comprises, for example, 4 to 18% by volume of nitrogen, especially 6 to 16% by volume and more preferably 8 to 12% by volume of nitrogen. The gas mixture M-2 further comprises, for example, 0.01 to 5% by volume of oxygen, especially 0.5 to 3% by volume and more preferably 1.0 to 2.0% by volume of oxygen, and, for example, 0 to 1% by volume of argon, where the sum of the components of gas mixture M-2 adds up to 100% by volume.

It is possible that the gas mixture M-2 is recycled into a stage of the process. In such an embodiment, dinitrogen monoxide which is present in gas mixture M-2 can be recycled into the process in order to avoid yield losses.

The gas mixture M-2 is preferably recycled into step (A) of the process. The gas mixture M-2 is mixed with another gas mixture. Preference is given to recycling the gas mixture M-2 into step (A) in such a way that recovery of the dinitrogen monoxide which may be present in gas mixture M-2 is possible. It is therefore preferred that the gas mixture M-2 is mixed with a gas mixture which is sent to an absorption, especially with the gas mixture G-0 or gas mixture G-1. It is thus preferred to recycle gas mixture M-2 into step (i) or into step (iii) of step (A).

The oxidation of cyclopentene by means of dinitrogen monoxide or by means of a gas mixture comprising dinitrogen monoxide can generally be effected by all process regimes in which oxidation takes place. More particularly, both continuous process regimes and methods of reaction and batch reactions are possible. According to the invention, the reaction conditions for the oxidation of cyclopentene are selected such that a reaction takes place. Pressure and temperature can be selected accordingly.

The pressure is preferably within a range up to 500 bar, for example 1 to 320 bar, preferably 10 to 300 bar, especially 90 to 280 bar. The temperature is preferably within a range from 180 to 320° C., for example 200 to 300° C., especially 240 to 290° C.

The oxidation of cyclopentene can be performed in the presence of a suitable solvent. However, it is equally possible to perform the oxidation without the addition of a solvent.

Preference is given to conducting the oxidation of cyclopentene, through suitable selection of the pressure and of the temperature, such that no gas phase occurs in the reaction zone.

The reaction of cyclopentene and dinitrogen monoxide is preferably performed adiabatically.

An adiabatic reaction is understood to mean a reaction in which essentially no heat exchange takes place between reactor contents and environment during the reaction. In the context of the present invention, an adiabatic reaction is preferably understood to mean a reaction in which preferably less than 10%, more preferably less than 5%, of the heat generated is released to the environment.

The process is preferably performed in such a way that cyclopentene and dinitrogen monoxide are converted in a reactor thermally insulated from the environment, wherein the thermal energy generated in the exothermic reaction remains essentially within the reactor and is not removed to the outside. A suitable process is described, for example, in EP 08163319.0.

In an adiabatic process regime, the difference between the temperature of the products (T(out)) and the temperature of the reactants (T(in)) is defined as the adiabatic temperature increase (T(adiab)). In a preferred embodiment of the process, T(adiab) is between 10 and 140° C., more preferably between 20 and 125° C. and most preferably between 25 and 100° C.

The process can, for example, be performed in such a way that suitable parameters, for example the conversions of the individual reactants, which are in turn influenced by the residence time, by the inlet temperature of the reactant mixture (T(in)), by the reaction pressure and by the concentrations of the individual reactants in the reactant mixture, are established such that the heat of reaction generated by the reaction is the heat which is needed in order that the production mixture leaves the reactor with a temperature (T(out)) which is at least 10 K below the temperature at which the adiabatic induction time is exactly 24 hours. The adiabatic induction time as a function of temperature can be derived in a manner known per se from the data of DSC experiments with different heating rates.

It is possible that both reactants have the same inlet temperature or different inlet temperatures. What is relevant in the context of the present invention is the reactor inlet temperature of the reactant mixture, i.e. the temperature which is established when all reactant streams are mixed together.

In a preferred embodiment, the reactor inlet temperature of the reactant mixture (T(in)) is 170 to 270° C., more preferably 200 to 260° C., for example 220 to 250° C.

The temperature that the reactants have at the reactor inlet preferably also corresponds to the minimum temperature at which, in the process according to the invention, the desired conversion can still be achieved in an industrially implementable reactor size. The minimum temperature at which, in the process according to the invention, the desired conversion can still be achieved in an industrially realizable reactor size is therefore generally at least 170° C., preferably at least 200° C.

The maximum reactor outlet temperature (T(out)) of the product mixture at which the process can be performed is generally at most 340° C., preferably at most 320° C., more preferably at most 300° C. This maximum reactor outlet temperature (T(out)) is selected such that preferably no thermal decomposition of the product formed or of the unconverted reactants takes place.

The process is thus generally performed at a temperature of 170 to 340° C., preferably 200 to 320° C., the former temperature being the reactor inlet temperature (T(in)) of the reactant mixture and the latter temperature the reactor outlet temperature (T(out)) of the product mixture.

In a preferred embodiment, the process is performed at a reaction pressure of 60 to 500 bar, more preferably of 80 to 325 bar, more preferably of 90 to 180 bar, for example at 100 to 150 bar.

The process can be performed in such a way that the molar ratio between cyclopentene and dinitrogen monoxide has a suitable value such that the heat of reaction generated by the reaction is exactly the heat which, given an appropriate reactor inlet temperature (T(in)) of the reactant mixture and given full conversion of the reactant present in deficiency, preferably dinitrogen monoxide, gives rise to a reactor outlet temperature (T(out)) of the product mixture which is below the above-mentioned maximum temperatures of 340° C., preferably 320° C., more preferably 300° C.

In a preferred embodiment, the molar ratio of dinitrogen monoxide to cyclopentene is in the range from 0.02:1 to 0.3:1, more preferably from 0.05:1 to 0.25:1 and most preferably from 0.08:1 to 0.2:1. This "molar ratio of the reactants" is understood to mean the quotient of the amounts of the reactants.

In a further preferred embodiment, the conversion based on dinitrogen monoxide in the process is in the range from 80 to 100%, more preferably from 90 to 99%, most preferably from 90 to 96%.

The process can be performed in all reactors which are known to those skilled in the art and are suitable for an adiabatic reaction regime, for example in a tubular reactor. In order to ensure an adiabatic reaction regime, it is, for example, necessary that the reactor is insulated sufficiently from the environment, such that essentially no heat of reaction is released to the environment and is thus no longer available to the actual reaction. In a particularly preferred embodiment, the heat generated by the reaction is discharged from the reactor by the product stream.

It is also possible to use a plurality of reactors, which may be connected in parallel or in series.

The reactor chamber of the usable reactor may be empty or may, if appropriate, be segmented by suitable internals. In general, the reactor has a flow profile suitable for an adiabatic reaction. In the reactor for use, preferably essentially no backmixing takes place. The reactor preferably has a residence time distribution which corresponds to that of a stirred tank cascade with at least 8 stirred tanks. The reactor more preferably has a residence time distribution which corresponds to that of a stirred tank cascade with at least 12 stirred tanks. The flow profile which is preferred in the process for the reaction mixture depends on the reactor used and can, if appropriate, be adjusted accordingly by suitable internals known to those skilled in the art, for example perforated plates, or by filling the reactor with a suitable packed bed.

Preference is given to using a tubular reactor with a length to diameter ratio greater than 1. The reactor more preferably comprises at least perforated plates to reduce backmixing.

It is possible that the reactor is operated in a recumbent or upright position, preferably upright. The flow of the reaction mixture through an upright reactor may be from the bottom upward or from the top downward, Preference is given to performing the process in an upright reactor through which the reaction mixture flows from the bottom upward.

A reactor particularly suitable for the continuous process regime is, for example, a tubular reactor which is preferably sufficiently insulated. Appropriate tubular reactors are known to those skilled in the art.

It is possible that the reactant streams are fed separately to the reactor. It is also possible and preferred in accordance with the invention that the reactant streams are fed to the reactor in already premixed form.

The reactant streams or at least a portion of the reactant streams used, for example 70 to 95%, can be preheated before the reaction by all processes known to those skilled in the art to a temperature of preferably 170 to 270° C., more preferably 200 to 260° C., for example 220 to 250° C., for example by means of an external heat source, for example steam, in a heat exchanger known to those skilled in the art, which functions as a preheater. The reactant streams are preferably preheated outside the reactor in a suitable heat exchanger.

The thermal energy needed to preheat the reactant streams is preferably withdrawn at least partly, preferably fully, from the reactor output, i.e. from the hot product stream of the process. For this purpose, at least a portion of the product stream is contacted with at least a portion, for example 70 to 95%, of the reactant mixture in a heat exchanger, for example a countercurrent heat exchanger.

The temperature of the stream supplied to the reactor can, for example, be adjusted via the proportion of reactant stream which is preheated by means of such a heat exchanger.

The product stream obtained from the process has a reactor outlet temperature (T(out)) of generally at most 340° C., preferably at most 320° C. and more preferably at most 300° C. After being contacted with the reactant stream, the product stream generally has a temperature of 150 to 220° C., preferably 170 to 200° C., for example 180 to 190° C. The reactant stream is heated to generally 180 to 280° C., preferably 240 to 275° C., for example 250 to 260° C.

In this process, the product stream obtained is preferably a reaction mixture which comprises at least cyclopentanone and nitrogen. In addition to these desired products, for example, unconverted reactants and/or by-products are present in the mixture.

The cyclopentanone obtained or the reaction mixture comprising cyclopentanone obtained in this way can in principle be processed further in the form obtained. Equally, the resulting mixture can, however, also be worked up by all suitable processes for obtaining cyclopentanone. Particular preference is given to distillative workup methods.

After the reaction of cyclopentene with $N_2O$, the reactor contents are cooled and decompressed, it being possible to cool and decompress in any sequence and in one or more stages. It is also possible in the context of the present invention to cool and decompress stepwise. This already removes most of the nitrogen formed and of the unconverted $N_2O$ as offgas. The liquid organic components are then subjected to a distillation in order to recover unconverted cyclopentene.

This workup may comprise one or more purification steps, for example at least one distillation, but preferably at least one one-stage evaporation, for example to remove $N_2$ and unconverted dinitrogen monoxide, and at least one distillation, more preferably at least one one-stage evaporation and at least two distillation steps.

In the work-up, the cyclopentanone product is separated from unconverted cyclopentene and any cyclopentane present in the reaction mixture.

This involves first decompressing the resulting mixture in at least one suitable vessel to a pressure which is generally below the reaction pressure, for example to a pressure of 1 to 20 bar, preferably 14 to 18 bar. In a preferred embodiment, the mixture is cooled in a suitable heat exchanger before this decompression.

The workup preferably further comprises at least one distillation step in a suitable distillation column, preferably in a recycle column. A suitable process is described, for example, in EP 08163319.0.

A suitable example is a recycle column which has 30 to 50, preferably 35 to 45, theoretical plates. The feed is generally in the middle part of the column. In a further preferred embodiment, for example, cyclopentene is obtained in a side draw of the column.

Since low boilers also form in oxidation of cyclopentene with $N_2O$, for example acetone and ethylene (from the oxidation of 2-methyl-2-butene which is present as an impurity in cyclopentene), the return cyclopentene is preferably not withdrawn as a top stream but as a side stream. The top stream withdrawn is merely a small purge stream which serves as a discharge for low boilers, for example acetone. The distillation is performed at slightly elevated pressure, for example at 2 to 6 bar, especially at 3 to 5 bar, preferably at about 4 bar. The column has a total of, for example, 30 to 50, preferably, for example, 35, 36, 37, 38, 39, 40, 41, 42, 43 or 44 plates, more preferably 38, 39 or 40 plates. Below the inflow point of the feed are, for example, 17 to 22 plates, preferably 18, 19 or 20 plates. Between the inflow point of the feed and side draw are, for example, 7 to 12 plates, preferably 8, 9 or 10 plates, and between side draw and top are, for example, 8 to 14 plates, preferably 10, 11 or 12 plates. The column is adjusted such that cyclopentane accumulates in the circulation. At the steady state, the return cyclopentene, which is preferably removed in the side draw, comprises between 40 and 60% by weight of cyclopentane. In the bottom of the column, "crude" cyclopentanone is removed with a purity of >80% by weight, preferably >90% by weight. This stream also comprises cyclopentanone and other by-products from the oxidation.

A suitable stream comprising unconverted cyclopentene which has been distilled off can then, for example, be recycled and be reused in the process alone or after addition of a suitable mixture comprising cyclopentene.

The distillation in the recycle column is effected, for example, at a pressure of 1.0 to 7.0 bar, preferably of 2.0 to 6.0 bar, for example of 3.5 to 5.0 bar.

The distillation in the recycle column is effected, for example, at a temperature of 80 to 200° C., preferably of 90 to 190° C. The temperature in the bottom of the column is, for example, in the range from 150 to 200° C., preferably from 160 to 185° C.; the temperature above the bottom of the column is, for example, in the range from 80 to 110° C., preferably from 90 to 105° C.

In a further embodiment of the workup, unconverted cyclopentene is obtained in a mixture with further hydrocarbons, for example cyclopentane, for example as a mixture comprising 20 to 98% by weight, preferably 30 to 80% by weight, more preferably 40 to 60% by weight, based in each case on the mixture, of cyclopentene, and 2 to 80% by weight, preferably 20 to 70% by weight, more preferably 40 to 60% by weight, based in each case on the mixture, of at least one further hydrocarbon, for example a saturated hydrocarbon, especially cyclopentane, This mixture may comprise further components, for example hydrocarbons, product or by-product from the reaction and/or linear olefins, up to a total content of up to 1.5% by weight, preferably up to 1.0% by weight, based in each case on the mixture.

In a further preferred embodiment of the workup, low-boiling components are obtained at the top of the recycle column, for example C5 hydrocarbons such as n-pentane, 2-methyl-2-butene, cis-2-pentene and trans-2-pentene.

In a further embodiment of the workup, cyclopentanone is obtained in the bottom of the recycle column, in a preferred embodiment with a purity of up to 95% by weight, preferably up to 92% by weight, based in each case on the bottoms fraction.

It is also possible that the workup, in addition to the one-stage evaporation and the first distillation, preferably the distillation in a recycle column, comprises a further distillation. For instance, it is possible that the product can be purified further by distilling the cyclopentanone, for example in one or more columns, preferably in two columns or more preferably in a dividing wall column.

The product obtained from the distillation in the recycle column is purified, for example, at a pressure of 0.5 to 3 bar, preferably 0.8 to 2 bar, for example 1.0 to 1.2 bar.

The product obtained from the distillation in the recycle column is purified, for example, at a temperature of 100 to 200° C., preferably 110 to 180° C., for example 120 to 170° C.

For example, the product obtained from the distillation in the recycle column is purified, for example, in a dividing wall column at a pressure of 0.5 to 3 bar, preferably 0.8 to 2 bar, for example 1.0 to 1.2 bar, and at a temperature of 100 to 200° C., preferably 110 to 180° C., for example 120 to 170° C.

The bottom product from the first column is then worked up further by distillation in order to obtain pure cyclopentanone therefrom. For this distillative purification of cyclopentanone, two columns can be used. In the first column with, for example, 17 to 25 plates, preferably 19 to 23 plates, especially 20, 21 or 22 plates, the low-boiling secondary components are removed via the top at 0.9 to 1.3 bar, preferably 1.0 to 1.2 bar, more preferably at 1.1 bar. The bottom product is then distilled in a further column with, for example, 30 to 50 plates, preferably 35 to 44 plates, especially 36, 37, 38, 39 or 40 plates, at 0.9 to 1.3 bar, preferably 1.0 to 1.2 bar, more preferably at 1.1 bar, to obtain pure cyclopentanone via the top and remove high-boiling impurities via the bottom. It is particularly preferred, however, when the distillative purification of cyclopentanone is performed in a single dividing wall column.

The pure cyclopentanone which is obtained from the side draw has a purity of at least 99% by weight, preferably at least 99.5% by weight and more preferably at least 99.8% by weight.

The top product obtained is a stream which comprises all low-boiling secondary components but not more than 0.1% by weight of cyclopentanone, preferably not more than 0.01% by weight of cyclopentanone. The main components present therein are cyclopentane, 4-pentenal, 3-methyl-2-butanone (from the oxidation of 2-methyl-2-butene), cyclopentene oxide and cyclopentene (in each case >5% by weight). Secondary components also present in this stream are acetone, 2-methyl-2-butene, 2-methyl-1-butene, 3-methylpentane, pivalaldehyde (from the oxidation of 2-methyl-2-butene), methylcyclopentane, diethylketone (from the oxidation of 2-pentene), cyclopropylacetaldehyde, cyclobutylcarbaldehyde, 2-methyl-3-pentanone (from the oxidation of 2-methyl-2/3-hexene) and cyclopentenone.

The bottom product obtained is a stream comprising high-boiling impurities, This stream also comprises not more than 50% by weight of cyclopentanone, preferably not more than 40% by weight of cyclopentanone. The main components present in this stream are cyclopentene dimers (cyclopentylcyclopentenes) and cyclopentanone dimers.

The top stream of this column, which comprises between 10 and 50% by weight of 4-pentenal, can be used either directly or after further treatments as mixture (G) in the process according to the invention for preparing 4-pentenoic acid.

This stream is preferably concentrated further by distillation before the oxidation. Very particular preference is given to substantially removing the cyclopentene and cyclopentane low boilers present therein before the oxidation.

The mixture (G) obtained in this way, comprising 4-pentenal, 3-methyl-2-butanone and cyclopentene oxide, is especially suitable for preparing 4-pentenoic acid.

In a further aspect, the present invention therefore also relates to the use of a mixture (G) comprising 4-pentenal, 3-methyl-2-butanone and cyclopentene oxide for preparing 4-pentenoic acid.

As stated, an especially suitable mixture (G) is one comprising 4-pentenal, 3-methyl-2-butanone and cyclopentene oxide, which is obtained as a by-product of the oxidation of cyclopentene to cyclopentanone by means of dinitrogen monoxide.

In a further embodiment, the present invention therefore also relates to the use of a mixture (G) comprising 4-pentenal, 3-methyl-2-butanone and cyclopentene oxide for preparing 4-pentenoic acid as described above, wherein the mixture (G) is obtained as a by-product of the oxidation of cyclopentene to cyclopentanone by means of dinitrogen monoxide.

Thus, the present invention includes the following embodiments:

1. A process for preparing 4-pentenoic acid, at least comprising step (a)
   (a) oxidizing a mixture (G) comprising 4-pentenal, 3-methyl-2-butanone and cyclopentene oxide.
2. The process according to embodiment 1, wherein the mixture (G) comprises 10 to 90% by weight of 4-pentenal.
3. The process according to embodiment 1 or 2, wherein an oxygenous gas mixture is used as the oxidizing agent for the oxidation in step (a).
4. The process according to any of embodiments 1 to 3, wherein the oxidation in step (a) is performed in the presence of a solvent.
5. The process according to any of embodiments 1 to 4, wherein the oxidation in step (a) is performed in the presence of a solvent selected from the group consisting of 4-pentenoic acid, 2-ethylhexanoic acid, isononanoic acid, propylheptanoic acid and neodecanoic acid.
6. The process according to any of embodiments 1 to 5, wherein the oxidation in step (a) is performed without addition of a catalyst.

7. The process according to any of embodiments 1 to 6, wherein the mixture (G) is obtained as a by-product of the oxidation of cyclopentene to cyclopentanone.
8. The process according to embodiment 7, wherein cyclopentene is oxidized to cyclopentanone in the presence of dinitrogen monoxide.
9. The use of a mixture (G) comprising 4-pentenal, 3-methyl-2-butanone and cyclopentene oxide for preparing 4-pentenoic acid.
10. The use according to embodiment 9, wherein the mixture (G) is obtained as a by-product of the oxidation of cyclopentene to cyclopentanone by means of dinitrogen monoxide.

DESCRIPTION OF FIGURES

FIG. 1 shows a schematic of the construction of a plant for reacting cyclopentene with dinitrogen monoxide, comprising a reactor (R), a flash vessel (F) and a distillation column (D). $N_2O$ is metered into the reactor via stream (1); the fresh cyclopentene feed is metered in via stream (2). Stream (2) is mixed with stream (8) (return cyclopentene) in order to obtain a stream (3). Stream (4) corresponds to the reactor output which is fed to the flash vessel. A gaseous stream (5) and a liquid phase (6) are withdrawn from the flash vessel. Stream (6) is fed to the distillation column (D). Stream (7) is obtained as the bottom product from the distillation column, stream (8) as the side draw product and stream (9) as the top stream.

The invention is illustrated in detail hereinafter with reference to examples.

EXAMPLES

Example 1

Reaction of Cyclopentene with Dinitrogen Monoxide

The experiment according to Example 1 was performed in a plant with a construction according to schematic FIG. 1.

Through stream (2), the fresh cyclopentene feed was metered in at 116.4 g/h. This originated from the distillation of a $C_5$ cut from a steamcracker and had the following composition (% by weight): cyclopentene (approx. 95.1%), cyclopentane (approx. 3.4%), 2-methyl-2-butene (approx. 1.2%).

This stream was first mixed with stream (8) (return cyclopentene) in order to obtain a stream (3) which had the following composition: cyclopentene (approx. 46.3%), cyclopentane (approx. 51.9%), 2-methyl-2-butene (approx. 0.9%), 2,2-dimethylbutane (approx. 0.81%).

This stream was then metered to the reactor (R) with a metering pump (flow rate: approx. 2076 g/h). Through stream (1), liquid $N_2O$ ($N_2O$ content >99.8% by volume, from Messer Griesheim) was metered to the reactor at approx. 74 g/h. The molar cyclopentene:$N_2O$ ratio in the reactor feed was 0.11 mol/mol. The reactor consisted of a tube (external diameter=60.3 mm, wall thickness=2.4 mm, length=approx. 4 m). The reaction volume was (minus the volume of random packings), including connecting pieces, approx. 8 l in total.

The tube was provided with an insulating jacket with an additional three-piece support heater which was set to (from the bottom) 256° C., 275° C. and 317° C. The cyclopentene conversion in straight pass was 11% and the $N_2O$ conversion approx. 96%. The reactor output (4) was, downstream of the pressure regulator, decompressed to 1 bar in two steps with two flash vessels (F) operated at 10 bar and 1 bar, and cooled.

The gaseous components (stream (5)) were removed, and hydrocarbons present therein were very substantially condensed out in a downstream cooler (operated at +5° C., not shown in the diagram).

The liquid phase (6) was separated in a distillation column (D) (bubble-cap tray column with 20 trays and liquid side draw). The bottom product (7) obtained was 138.7 g/h of a stream with the following composition: cyclopentanone (approx. 95.3% by weight), cyclopentane (approx. 0.8% by weight), 4-pentenal (approx. 1.3% by weight), cyclopentene oxide (approx. 0.37% by weight), cyclopentene dimers (approx. 0.53% by weight), cyclopentene (approx. 0.08% by weight).

The side draw product, stream (8), which comprised 45.6% cyclopentene, was recycled to the reactor via stream (3).

At the top of the column, via the top stream (9), only very small amounts of low boilers (e.g. ethylene and acetaldehyde from the oxidation of 2-methyl-2-butene) were discharged.

Example 2

Distillative Purification of Cyclopentanone to Obtain a 4-Pentenal-Rich Stream

From the plant described in Example 1, the product from a prolonged run was collected. For the distillation, a total of 35 kg were collected, which had the following composition: cyclopentanone (95.5% by weight), cyclopentane (1.0% by weight), 4-pentenal (1.3% by weight), cyclopentene oxide (0.4% by weight), 3-methyl-2-butanone (0.3% by weight), cyclopentene dimers (0.5% by weight), 2-cyclopentylcyclopentanone (0.5% by weight), 3-methylpentane (0.1% by weight) and cyclopentene (0.1% by weight), in addition to a series of further by-products with concentrations each below 100 ppm.

This mixture was distilled in a continuously operated laboratory dividing wall column. The column had a diameter of 43 mm and a packing height of 2.5 m and was provided with a packing (Montz A3 1000). Between 0.85 and 2.10 m above the lower edge of the packing, the column was divided by a central dividing wall. The product feed was 1.0 m above the lower edge of the packing. The side draw was 1.3 m above the lower edge of the packing, but on the other side of the dividing wall. The distillation was performed at a top pressure of 0.6 bar. The feed (330 g/h) was preheated to boiling temperature before it was fed into the column. The reflux ratio was approx. 170. The distillation was performed continuously until the 35 kg of feed had been consumed.

In the side draw, pure cyclopentanone (average 313 g/h) was obtained with a purity of 99.9%.

At the top, in addition to a small amount of offgas, a liquid product was obtained (average 6 g/h), which had the following composition: 4-pentenal (52.6% by weight), cyclopentane (15.8% by weight), cyclopentene oxide (14.8% by weight), 3-methyl-2-butanone (10.4% by weight), 3-methylpentane (2.4% by weight), cyclopentene (1.7% by weight), methylcyclopentane (1.2% by weight), in addition to a series of further by-products with concentrations each below 1000 ppm.

From the distillation, a total of approx. 600 g of the top stream were obtained.

Example 3

Concentration of the Top Stream from Example 2

The top stream product from Example 2 was introduced into the boiler of a batch distillation column. The column used had a height of 0.5 m and was filled with metal Raschig rings. The distillation was carried out at standard pressure. Product was drawn off via the top until the top temperature rose above 73° C. The distillation was then stopped, the bottoms were cooled and the system was inertized with $N_2$. The distillate (approx. 120 g) was discarded.

The product remaining in the bottom was only slightly yellow-colored and comprised, according to GC analysis, 4-pentenal (67%), cyclopentene oxide (19%), 3-methyl-2-butanone (13%), in addition to a series of further by-products with concentrations each below 2000 ppm.

This product was stored under nitrogen and used without further treatment for the oxidation experiments.

Example 4

Oxidation of 4-pentenal (with $NaClO_2$)

A 1000 ml stirred flask was initially charged with 78.8 g (0.95 mol) of 4-pentenal in 370 ml of acetonitrile. Within 1.5 h, 64.7 g (0.95 mol) of aqueous hydrogen peroxide solution (50% by weight in water) and a solution of 107.4 g (0.95 mol) of sodium chlorite (technical grade, approx. 80%) in 400 ml of water were added dropwise in parallel at 25-40° C. The monophasic reaction mixture was stirred at 25° C. for a further 1.5 h. Subsequently, the mixture was extracted three times with 100 ml of dichloromethane. The pH of the phases was approx. 5-6. The organic phase was concentrated on a rotary evaporator.

58 g remained as the residue, which was purified by distillation. The yield of 4-pentenoic acid with a purity of 95% was 26%.

The sample of 4-pentenoic acid thus obtained was assessed for odor by means of a test with perfumer's smelling strips. The first odor impression was described as cheesy, reminiscent of butyric acid and acidulous. After 10 minutes, the odor impression was described as cheesy, smelling of propionic acid. After 1 h, the impression was described as cheesy, somewhat acidulous.

In addition, the sample was subjected to a headspace test. To this end, 1 ml of the sample was mixed with 50 ml of water in a twist-off bottle and the closed bottle was left to stand for 10 minutes. Subsequently, it was opened and the gas phase was smelt. The odor impression was described as fruity and pleasant.

Example 5

Oxidation of 4-Pentenal (with $O_2$)

A thermostated bubble column with glass jacket (internal diameter=33 mm, height H=550 mm, provided at the bottom with a P160 glass frit and filled with glass Raschig rings (5×5 mm)) was charged with 151 g of 4-pentenal. Through a glass frit at the base of the bubble column, 5 l (STP)/h of oxygen (l (STP)–standard liters) were bubbled in. The temperature of the cooling medium in the jacket was set to 20° C. by means of an external thermostat. The headspace at the upper end of the bubble column was inertized by purging with nitrogen. After 24 hours, the reaction was stopped and the composition of the reaction output was determined by GC. The conversion of 4-pentenal was 49% and the selectivity for 4-pentenoic acid was approx. 82%.

The reaction output was worked up by distillation in order to obtain 4-pentenoic acid with a purity of 98.9% by weight.

The sample of 4-pentenoic acid thus obtained was assessed for odor by means of a test with perfumer's smelling strips. The first odor impression was described as acidulous, reminiscent of propionic acid and somewhat cheesy. After 10 minutes, the odor impression was described as slightly flowery, cheesy and acidulous. After 1 h, the impression was described as cheesy and reminiscent of propionic acid.

In addition, the sample was subjected to a headspace test. To this end, 1 ml of the sample was mixed with 50 ml of water in a twist-off bottle and the closed bottle was left to stand for 10 minutes. Subsequently, it was opened and the gas phase was smelt. The odor impression was described as fruity and somewhat dusty.

Example 6

Oxidation of Crude 4-Pentenal (with $O_2$)

The procedure was as in Example 5, except that, instead of 4-pentenal, the mixture of 4-pentenal (67%), cyclopentene oxide (19%), 3-methyl-2-butanone (13%) from Example 3 was used. 150 g thereof were introduced into the bubble column. The procedure was otherwise as in Example 5.

After a reaction time of 70 hours, the output was analyzed by means of GC. The conversion of 4-pentenal was 32% and the selectivity of 4-pentenoic acid was 82%. The conversions of cyclopentene oxide and 3-methyl-2-butanone were negligibly small (<5%), and it was not possible to detect any products derived therefrom (for example 3-hydroxy-3-methyl-2-butanone) in the GC. The active oxygen content (determined iodometrically) was only 5 g/kg of solution.

The reaction output was distilled, and it was possible to obtain 4-pentenoic acid with a content of 98% by weight. In terms of odor impression, the 4-pentenoic acid was comparable to that obtained in Example 5 from the oxidation of pure 4-pentenal.

This example shows that, even when the crude mixture is used, the oxidation of 4-pentenal is possible selectively and the quality of the 4-pentenoic acid obtained therefrom is not impaired.

The invention claimed is:

1. A process for preparing 4-pentenoic acid, at least comprising step (a)
   (a) oxidizing a mixture (G) comprising 4-pentenal, 3-methyl-2-butanone and cyclopentene oxide; wherein the oxidation in step (a) is performed without addition of a catalyst.

2. The process according to claim 1, wherein the mixture (G) comprises 10 to 90% by weight of 4-pentenal.

3. The process according to claim 1, wherein an oxygenous gas mixture is used as the oxidizing agent for the oxidation in step (a).

4. The process according to claim 1, wherein the oxidation in step (a) is performed in the presence of a solvent.

5. The process according to claim 1, wherein the oxidation in step (a) is performed in the presence of a solvent selected from the group consisting of 4-pentenoic acid, 2-ethylhexanoic acid, isononanoic acid, propylheptanoic acid and neodecanoic acid.

6. The process according to claim 1, wherein the mixture (G) is obtained as a by-product of the oxidation of cyclopentene to cyclopentanone.

7. The process according to claim 6, wherein cyclopentene is oxidized to cyclopentanone in the presence of dinitrogen monoxide.

* * * * *